US009968385B2

(12) United States Patent
Biedermann

(10) Patent No.: US 9,968,385 B2
(45) Date of Patent: May 15, 2018

(54) INSTRUMENT FOR USE WITH A POLYAXIAL BONE ANCHORING DEVICE AND SYSTEM INCLUDING THE INSTRUMENT AND A POLYAXIAL BONE ANCHORING DEVICE

(71) Applicant: Biedermann Technologies GmbH & Co. KG, Donaueschingen (DE)

(72) Inventor: Lutz Biedermann, VS-Villingen (DE)

(73) Assignee: BIEDERMAN TECHNOLOGIES GMBH & CO. KG, Donaueschingen (DE)

( * ) Notice: Subject to any disclaimer, the term of this patent is extended or adjusted under 35 U.S.C. 154(b) by 0 days. days.

(21) Appl. No.: 15/152,032

(22) Filed: May 11, 2016

(65) Prior Publication Data

US 2016/0331419 A1  Nov. 17, 2016

Related U.S. Application Data

(60) Provisional application No. 62/160,474, filed on May 12, 2015.

(30) Foreign Application Priority Data

May 12, 2015 (EP) .................................. 15 167 425

(51) Int. Cl.
*A61B 17/88* (2006.01)
*A61B 17/70* (2006.01)

(52) U.S. Cl.
CPC ...... *A61B 17/7082* (2013.01); *A61B 17/7037* (2013.01); *A61B 17/8891* (2013.01)

(58) Field of Classification Search
CPC ............ A61B 17/7082; A61B 17/7037; A61B 17/8891

(Continued)

(56) References Cited

U.S. PATENT DOCUMENTS 7,588,575 B2 * 9/2009 Colleran ................ A61B 5/103
606/252
7,666,189 B2 * 2/2010 Gerber ............... A61B 17/7074
606/104

(Continued)

OTHER PUBLICATIONS

European Search Report dated Nov. 16, 2015 for Application No. 15167425.6 (10 pages).

*Primary Examiner* — Pedro Philogene
*Assistant Examiner* — David C Comstock
(74) *Attorney, Agent, or Firm* — Lewis Roca Rothgerber Christie LLP

(57) ABSTRACT

An Instrument for use with a polyaxial bone anchoring device is provided, where the polyaxial bone anchoring device includes a receiving part for receiving a rod and for accommodating a head of a bone anchoring element. The head can be clamped by exerting a pressure force onto it via a clamping element and the pressure force can be adjusted using the instrument. The instrument includes a first member having a first engagement portion configured to engage the receiving part in a positive-fit manner. The instrument also includes a second member having a front end and a second engagement portion configured to engage the clamping element and apply torque to the clamping element. In a first configuration, the second member is axially displaceable along a longitudinal axis relative to the first member and is restricted from rotational movement. In a second configuration, the second member is rotatable with respect to the first member.

20 Claims, 6 Drawing Sheets

(58) Field of Classification Search
USPC ......... 606/266, 270, 269, 279, 305, 308, 99, 606/104, 86 A
See application file for complete search history.

(56) References Cited

U.S. PATENT DOCUMENTS

| | | | |
|---|---|---|---|
| 8,414,588 B2 * | 4/2013 | Stad | A61B 17/7085 606/246 |
| 8,926,671 B2 | 1/2015 | Biedermann et al. | |
| 2004/0147937 A1 | 7/2004 | Dunbar, Jr. et al. | |
| 2006/0036244 A1 | 2/2006 | Spitler et al. | |
| 2011/0004222 A1 | 1/2011 | Biedermann et al. | |
| 2014/0188173 A1 | 7/2014 | Mishra et al. | |

* cited by examiner

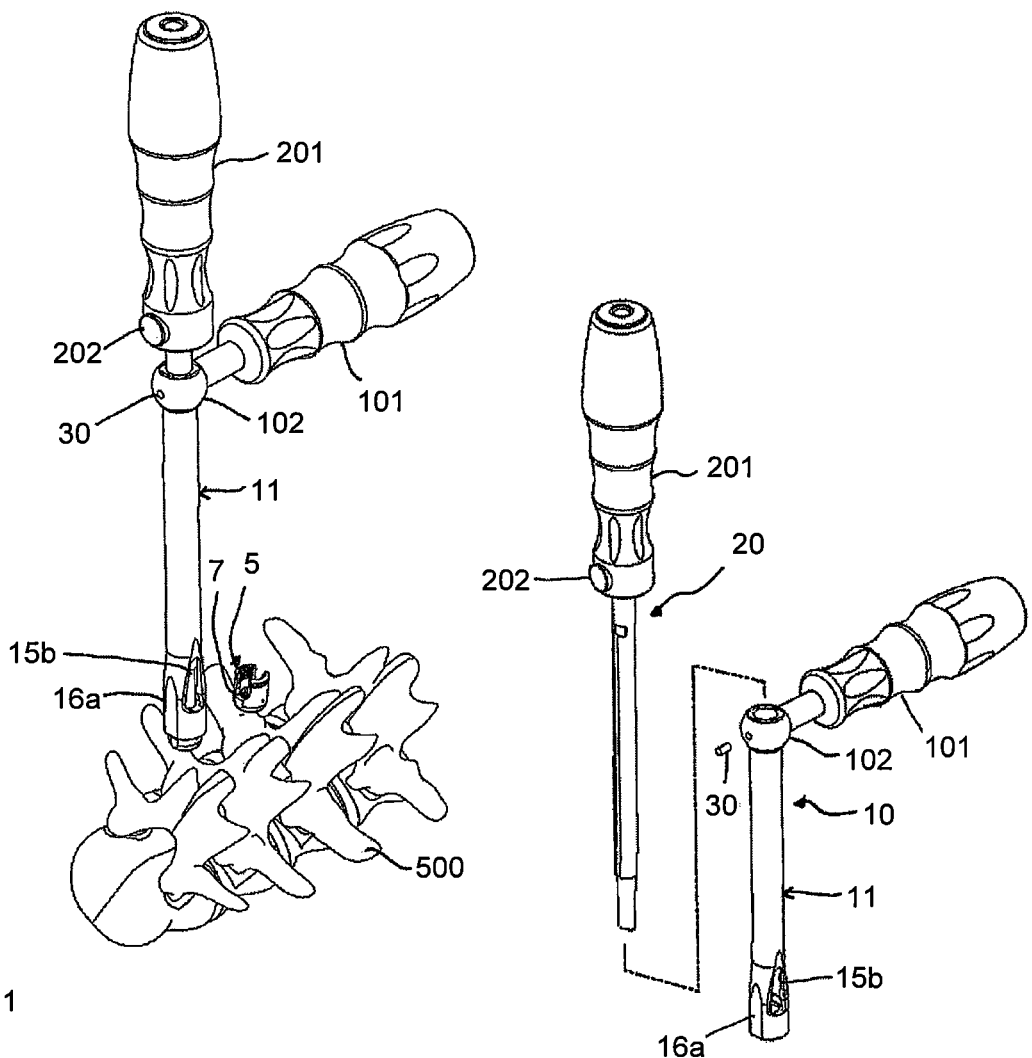
Fig. 1
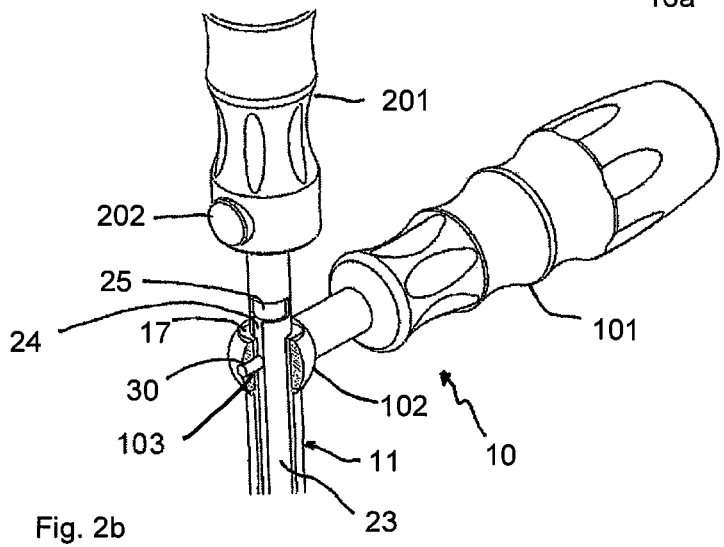
Fig. 2a
Fig. 2b

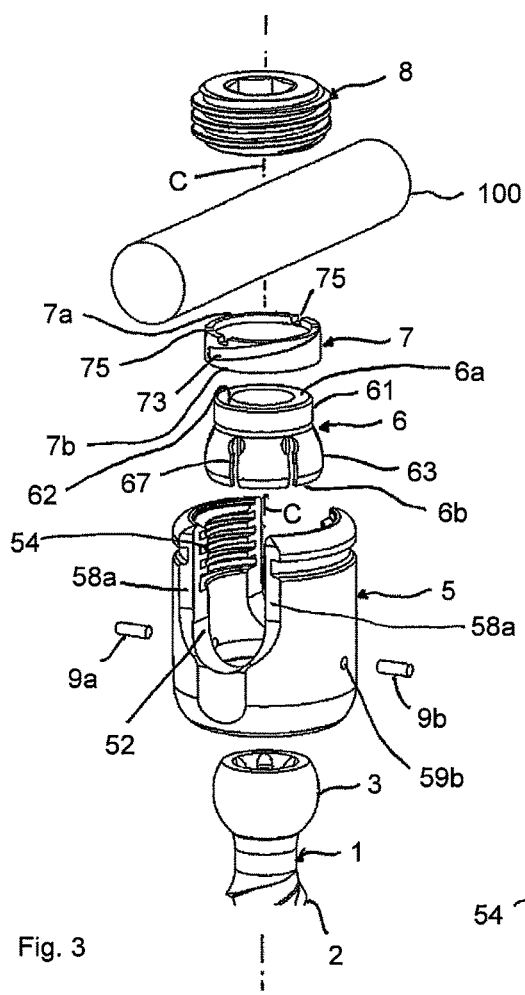
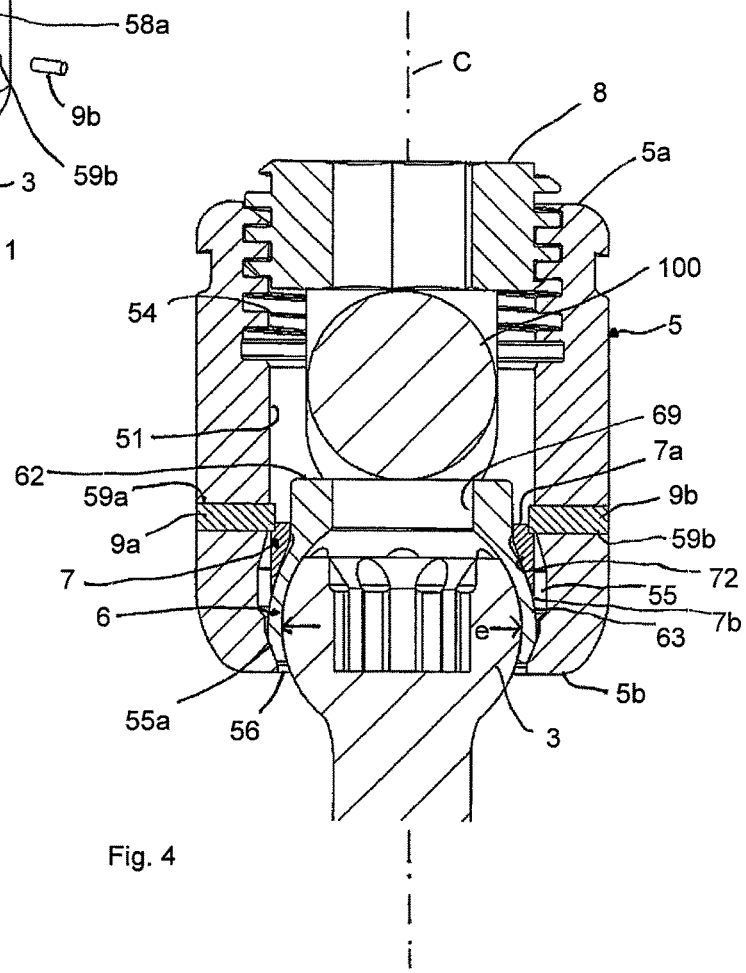
Fig. 3
Fig. 4

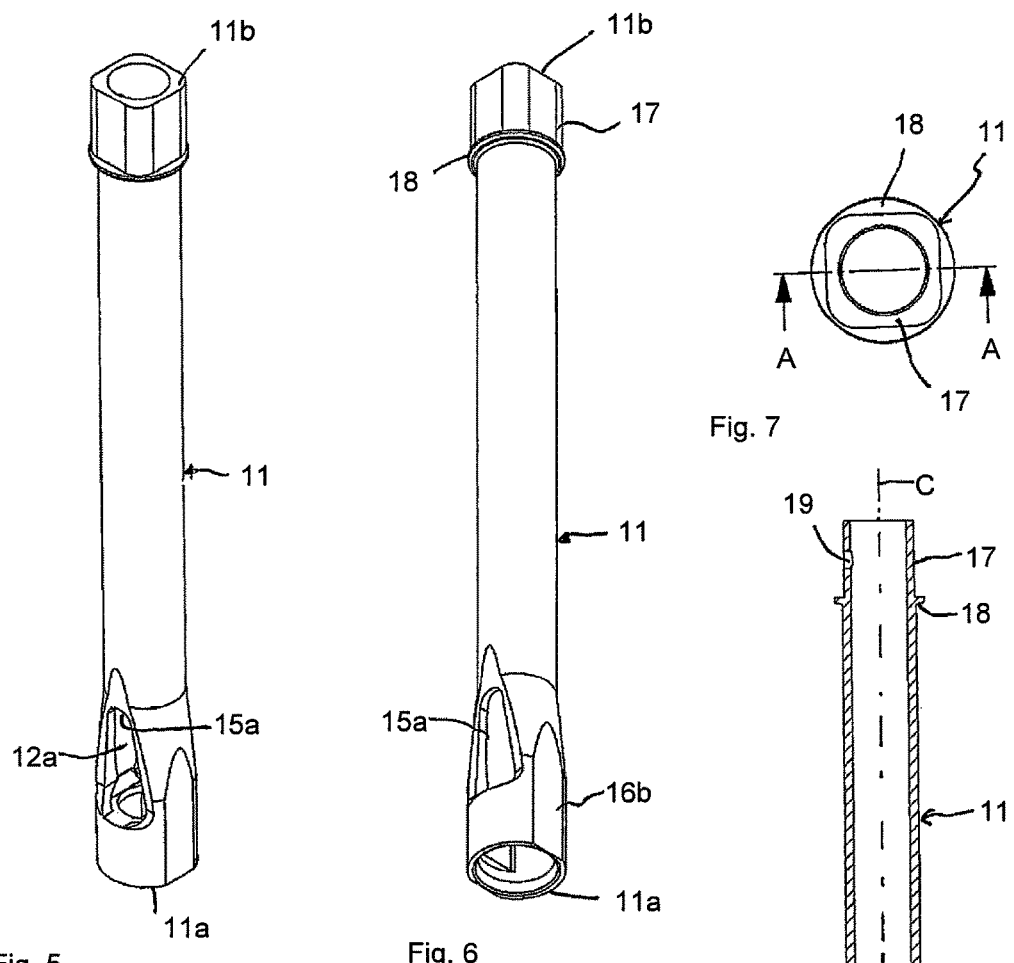
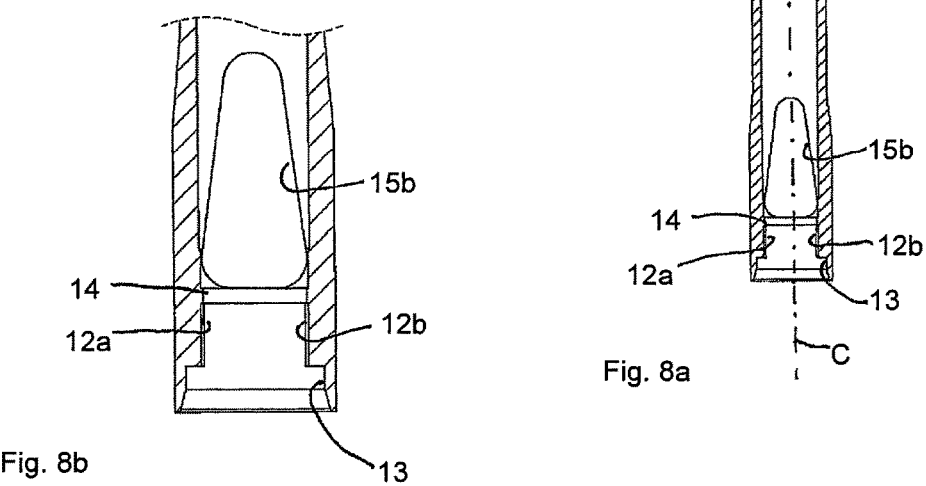

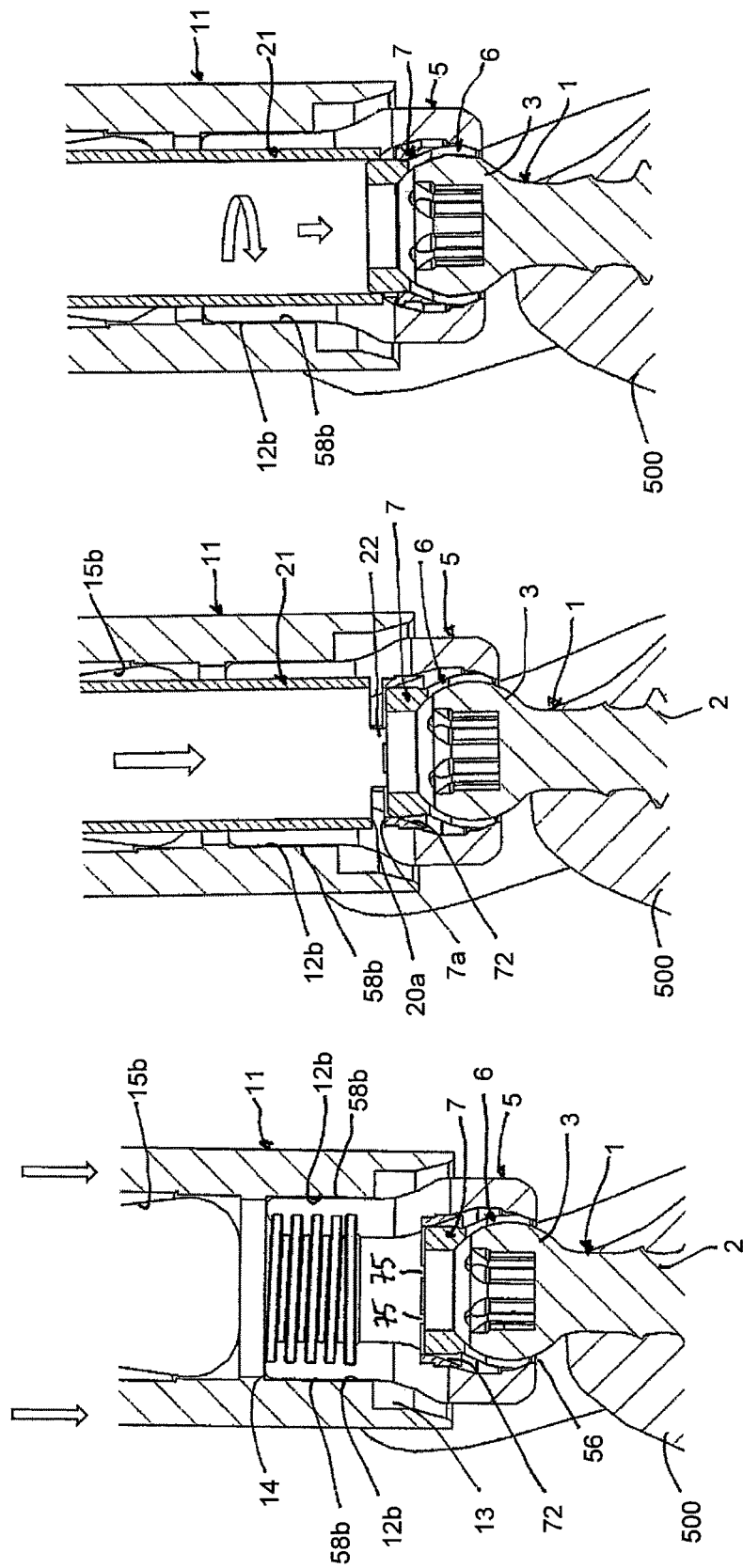

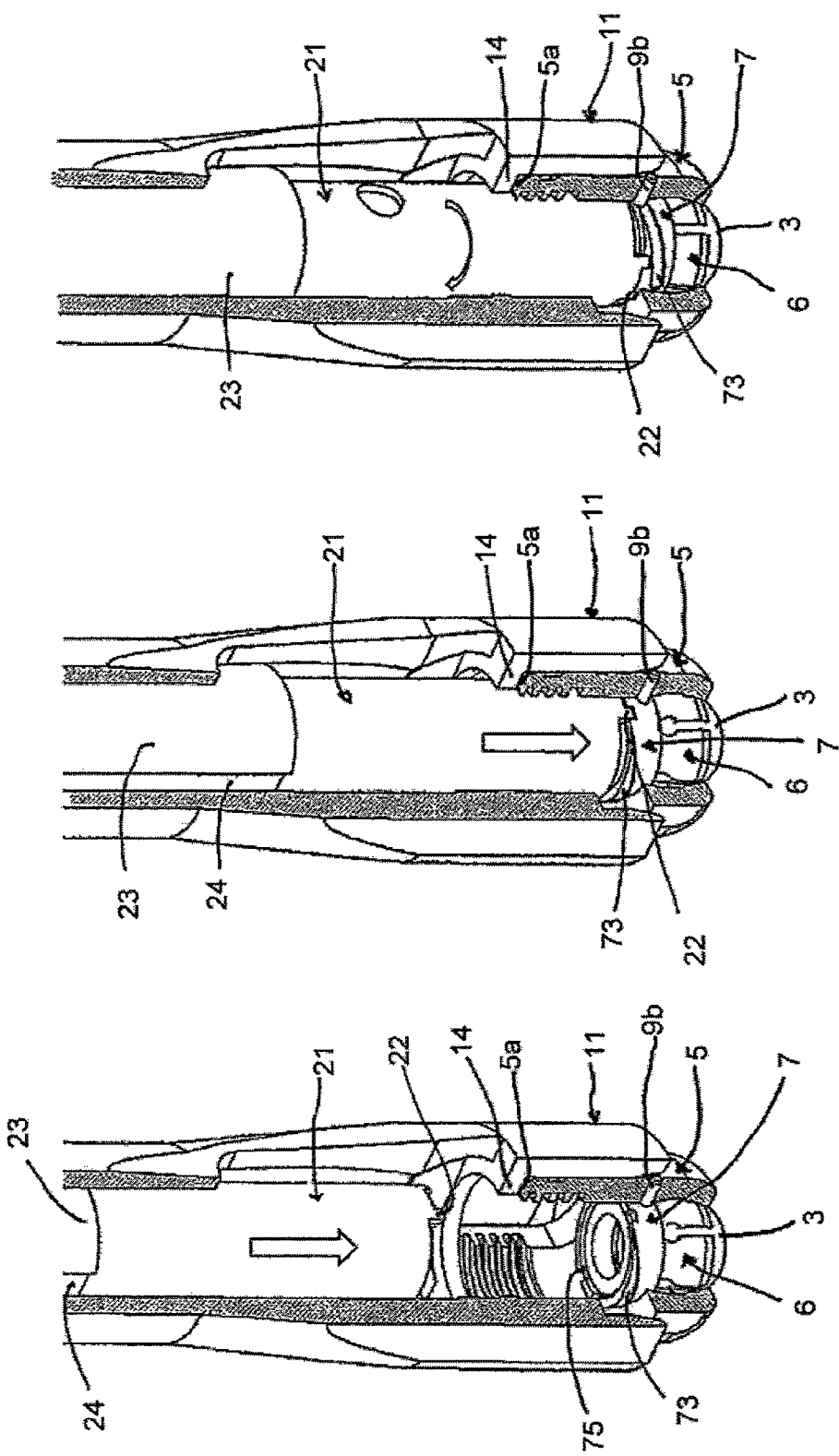

INSTRUMENT FOR USE WITH A POLYAXIAL BONE ANCHORING DEVICE AND SYSTEM INCLUDING THE INSTRUMENT AND A POLYAXIAL BONE ANCHORING DEVICE

CROSS-REFERENCE TO RELATED APPLICATIONS

The present application claims the benefit of U.S. Provisional Application Ser. No. 62/160,474, filed May 12, 2015, the contents of which are hereby incorporated by reference in their entirety, and claims priority from European Patent Application EP 15 167 425.6, filed May 12, 2015, the contents of which are hereby incorporated by reference in their entirety.

BACKGROUND

Field

The present disclosure relates to an instrument for use with a polyaxial bone anchoring device and to a system including the instrument and a polyaxial bone anchoring device. The polyaxial bone anchoring device includes a receiving part for receiving a rod and for accommodating a head of a bone anchoring element. The head can be clamped by exerting a pressure onto it via a clamping element. The instrument includes a first member and a second member displaceable relative to the first member. The first member is configured to engage the receiving part in a positive-fit manner and the second member is configured to engage the clamping element to adjust the clamping force applied onto the head.

Description of the Related Art

A variety of tools for use with polyaxial bone anchors are known. US 2011/0004222 A1 describes a tool having a tubular counter-holding portion configured to engage a receiving part of a bone anchor, and a driven shaft extending through the counter-holding portion. The driven shaft is configured to engage a locking element of the bone anchor, for example a set screw. The locking element is tightened using the driven shaft while the receiving part is held with the counter-holding portion.

U.S. Pat. No. 8,926,671 describes a receiving part for receiving a rod and for coupling the rod to a bone anchoring element. The receiving part includes a receiving part body for accommodating a head of the bone anchoring element and a pressure element with a flexible portion to clamp an inserted head. The pressure element is movable along a longitudinal axis of the receiving part body from an insertion position where the head is insertable into the receiving part body to a pre-locking position where the head is clamped in the receiving part body by a pre-stress exerted by the pressure element. The pressure element is further movable to a locking position where the head is locked in the receiving part body. The pre-stress exerted by the pressure element allows a desired angular position of the bone anchoring element to be maintained relative to the receiving part by friction before the head of the bone anchoring element is finally locked.

SUMMARY

In-situ placement of a receiving part onto a bone anchoring element that has been already inserted into a bone or a vertebra may be advantageously facilitated by mounting the receiving part and a pressure element onto a head of the bone anchor with a low insertion force. However, if the insertion force is low, a pre-stress exerted on the head of the bone anchoring element by the receiving part and the pressure element may be too low for the further procedure of aligning the receiving part for inserting a rod.

Embodiments of the invention provide an instrument for use with a polyaxial bone anchoring device and a system of an instrument and an improved polyaxial bone anchoring device that facilitates handling during surgery.

In one or more embodiments, an instrument is provided that allows adjusting a friction force exerted on a head of a bone anchoring element in an easy manner during surgery. In particular, the instrument, in connection with a polyaxial bone anchoring device, allows an operator to manually adjust the friction force on the head manually by actuating an actuating member of the instrument with one hand while holding the receiving part with a holding member held by the other hand of the operator. Pivoting the receiving part relative to the bone anchor element with the holding member gives the surgeon immediate feedback of the friction force acting on the head. The instrument permits a precise adjustment of the desired friction force on the head by sensing the friction force with the surgeon's hands.

The instrument may be particularly useful for a polyaxial bone anchoring element of the bottom loading type, where the head of the bone anchoring element is inserted into the receiving part from a bottom end thereof. The receiving part can be placed on the head of the bone anchoring element in-situ, after a shank of the bone anchoring element has already been inserted into (i.e., anchored to) a bone. Hence, in one or more embodiments, an instrument for use with an in-situ type bottom loading bone anchoring element is provided, where the friction force acting on the head can be adjusted in-situ on a patient.

The holding member of the instrument may be connected to the receiving part in a positive-fit manner where a surface of the receiving part cooperates with a surface of the holding member to prevent rotation between the holding member and the receiving part.

The actuating member may be connectable to the holding member only in a specific position (e.g., orientation) relative to the holding member. In this position, an engagement portion of the actuating member is substantially aligned with an engagement portion of a clamping element of the polyaxial bone anchoring device such that the clamping element can be easily engaged by the engagement portion of the actuating member. Thereby, the procedure of locating the clamping element with the instrument is facilitated and the actuation of the clamping element can be performed quickly. Through use of the clamping element, the friction force on the head of the anchoring element can be increased by rotating the clamping element in one direction and can be decreased by rotating the clamping element in an opposite direction. The procedure of aligning a plurality of receiving parts for inserting a rod is considerably simplified by manual adjustment of the frictional clamping of the head before final locking.

BRIEF DESCRIPTION OF THE DRAWINGS

Further features and advantages will become apparent from the description of embodiments by means of the accompanying drawings. In the drawings:

FIG. 1 shows a perspective view of an embodiment of an instrument together with a portion of a spinal column and an inserted polyaxial bone anchoring device;

FIG. 2a shows an exploded perspective view of the instrument of FIG. 1;

FIG. 2b shows an enlarged view of a detail of FIG. 2a;

FIG. 3 shows an exploded perspective view of a polyaxial bone anchoring device according to an embodiment;

FIG. 4 shows a cross-sectional view of the polyaxial bone anchoring device of FIG. 3, the cross-section taken in a plane perpendicular to the rod axis;

FIG. 5 shows a perspective view from above an outer tubular member of the instrument of FIGS. 1 to 2b;

FIG. 6 shows a perspective view from below the outer tubular member of FIG. 5;

FIG. 7 shows a top view of the outer tubular member of FIGS. 5 and 6;

FIG. 8a shows a cross-sectional view of the outer tubular member of FIGS. 5 to 7, the cross-section taken along line A-A in FIG. 7;

FIG. 8b shows a cross-sectional view of an enlarged portion of a front end of the outer tubular member shown in FIGS. 5 to 8a;

FIG. 10b shows a perspective view of an enlarged portion of a front end of the inner member of FIGS. 9 and 10a;

FIGS. 11a to 11c show cross-sectional views of steps of mounting the instrument to a polyaxial bone anchoring device with the bone anchoring element already inserted into a bone, the cross-section taken in a plane containing the rod axis; and FIGS. 12a to 12c show partial cross-sectional views of steps of mounting the instrument to a polyaxial bone anchoring device.

DETAILED DESCRIPTION

Figures 9, 10A:
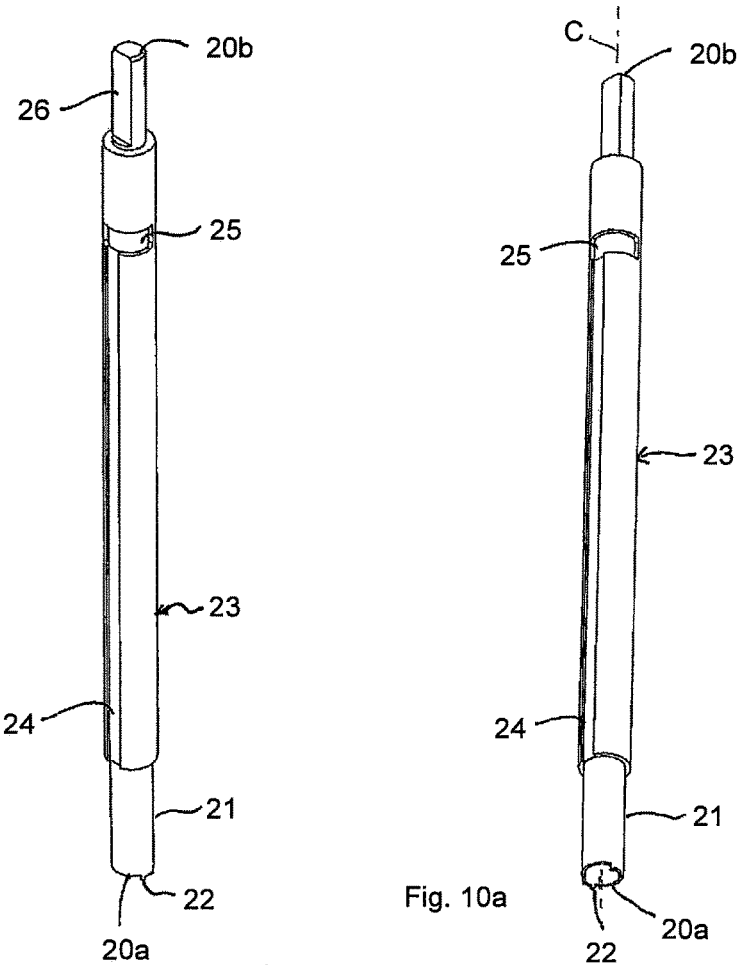
FIG. 9 shows a perspective view from above an inner member of the instrument of FIGS. 1 to 2b.
FIG. 10a shows a perspective view from below the inner member of FIG. 9.

Referring to FIGS. 1 to 2b, and instrument according to an embodiment includes a first member 10 and a second member 20 insertable into the first member 10. The first member 10 is configured to engage a receiving part 5 of a polyaxial bone anchoring device. In FIG. 1, the receiving part 5 is pivotably connected to a bone anchoring element that has been already inserted into a pedicle of a vertebra 500 prior to being connected to the receiving part 5. As described more fully below, a portion of the second member 20 is configured to engage and rotate a clamping element 7 provided in the receiving part 5.

Next, an embodiment of a polyaxial bone anchoring device that is used with the instrument will be described with reference to FIGS. 3 and 4. The polyaxial bone anchoring device includes a bone anchoring element 1, for example in the form of a bone screw having a threaded shaft 2 for anchoring to a bone and a head 3 that may be spherically segment-shaped. The bone anchoring device further includes the receiving part 5 for receiving a rod 100 to connect the rod 100 to the bone anchoring element 1. As described in more detail below, the head 3 of the bone anchoring element 1 is inserted into the receiving part 5 and into a pressure element 6 arranged in the receiving part 5. The pressure element 6 exerts a pressure force on the head 3 that has been inserted therein to clamp and finally lock the head 3 in the receiving part 5 (e.g., to lock an angular position of the head 3 relative to the receiving part 5). Additionally, a clamping element 7 is arranged in the receiving part 5 around a portion of the pressure element 6. The clamping element 7 is adapted to exert a compression force onto the pressure element 6 to increase the pressure force on the inserted head 3. The bone anchoring device further includes a locking element 8 for securing the rod 100 in the receiving part 5 and for exerting a force to lock the head 3 in the receiving part 5. The locking element 8 may be, for example, a set screw.

The receiving part 5 includes a first end 5a, a second end 5b opposite the first end 5a, and an axis of symmetry C passing through the first end 5a and the second end 5b. A passage 51 is provided that extends from the first end 5a to the second end 5b and is substantially rotationally symmetric about the axis of symmetry C. In a first region adjacent to the first end 5a, the receiving part 5 has a substantially U-shaped recess 52 that is symmetric with respect to the axis C, the recess 52 having a bottom directed toward the second end 5b. An internal thread 54 is formed adjacent or near the first end 5a that cooperates with the locking element 8.

A channel formed by the substantially U-shaped recess 52 is sized to receive the rod 100 therein, where the rod 100 is configured to connect a plurality of anchoring devices.

As can be seen in particular in FIG. 4, an accommodation space 55 is provided in a lower portion of the receiving part 5 with an inner diameter greater than an inner diameter of the passage 51 located in an upper section of the receiving part 5. The accommodation space 55 narrows toward the second end 5b in a narrowing portion 55a. The size of the accommodation space 55 is such that the head 3 of the bone anchoring element 1 and a lower portion of the pressure element 6 can be accommodated therein. The accommodation space 55 has an opening 56 at the second end 5b of the receiving part 5. A diameter of the opening 56 is greater than a greatest diameter of the head 3 such that the head 3 is insertable into the receiving part 5 through the opening 56 at the second end 5b. Flat outer surface portions 58a, 58b on the receiving part 5 on both sides of the U-shaped recess 52 (see FIGS. 3 and 11a) are configured to cooperate with flat surfaces on the instrument to provide a positive-fit connection between the receiving part 5 and the instrument.

Moreover, on each side of the channel formed by the U-shaped recess 52, bores 59a, 59b are provided for receiving pins 9a, 9b. The bores 59a, 59b are located at a position of approximately 90° with respect to an axis of the channel and respectively extend through the walls of the receiving part 5. As described below, the pins 9a, 9b are inserted into the bores 59a, 59b to engage the clamping element 7 in the receiving part 5.

Referring further to FIGS. 3 and 4, the pressure element 6 has a first end 6a and an opposite second end 6b. Adjacent to the first end 6a, the pressure element 6 has a first portion 61 that is substantially cylindrical and that has an outer diameter that is smaller than an inner diameter of the passage 51. A rod support surface 62 is provided at the first end 6a.

The pressure element 6 has a second cap-like portion 63 between the cylindrical first portion 61 and the second end 6b with a hollow interior having a shape adapted to receive the head 3 therein. In particular, the hollow interior of the second portion 63 has a spherical shape with a length in an axial direction of the pressure element 6 sufficient to accommodate a greatest diameter e of the head 3 therein (see FIG. 4). The second portion 63 of the pressure element 6 further includes at least one vertical slit 67, preferably a plurality of slits 67, open to the second end 6b and extend from a bottom of the second portion 63 almost up to the first portion 61 to render the second portion flexible. Further, the pressure element 6 includes a coaxial bore 69 for providing access to the head 3 of the bone anchoring element 1 by a screwdriver. The second portion 63 of the pressure element 6 is adapted to exert a pressure onto an inserted head 3 and to hold the head 3 by a frictional force between an inner surface of the hollow interior of the second portion 63 and an outer surface of the head 3. In other words, the flexible portion 63 fits tightly onto the head 3. Because the second portion 63 has a flexible wall, the second portion 63 can expand within the accommodation space 55 when the head 3 is inserted. The pressure element 6 can be pressed downward relative to the receiving part 5 such that the pressure element 6 enters the narrowing portion 55a of the receiving part 5. In such a configuration, the head 3 cannot be removed through the lower opening 56 in the receiving part 5 and the head is maintained at an angular position with respect to the receiving part 5 by a pre-stress acting onto the head 3 by the pressure element 6.

The clamping element 7 is a ring-shaped part with a first end 7a, an opposite second end 7b, and a substantially cylindrical outer shape. As depicted in FIG. 4, the clamping element 7 has an internal surface 72, which widens toward the second end 7b and which may be conical. The size of the internal surface 72 is such that the clamping element 7 can be mounted around the pressure element 6 with the internal surface 72 encompassing an upper region of the flexible second portion 63 of the pressure element 6. The clamping element 7 can be moved downward relative to the receiving part 5 such that the internal surface 72 contacts the outer surface of the flexible portion 63 such that pressure is exerted onto the flexible portion resulting in an increased compression of the head 3. Thereby, the frictional force between the head 3 and the pressure element 6 is increased.

An advancement structure including two opposite helical grooves 73, one of which is seen in FIG. 3, are provided on the outer surface of the clamping element 7. The helical grooves 73 are open toward the first end 7a and have a closed end toward the second end 7b. The size of the helical grooves 73 is such that the pins 9a, 9b can engage the grooves 73. The grooves 73 and the pins 9a, 9b permit the clamping element 7 to advance in the receiving part 5 toward the second end 5b by rotating the clamping element 7 around the axis of symmetry C. When the pressure element 6 and the clamping element 7 are inserted into the receiving part 5 with the grooves 73 engaged with the pins 9a, 9b, the closed ends of the grooves 73 prevent the clamping element 7 from escaping through the first end 5a of the receiving part 5. The advancement structure permits a stepless advancement of the clamping element 7 along the central axis C downwardly toward the second end 5b of the receiving part 5. A size of the helical groove 73 and the pins 9a, 9b and/or a pitch of the groove 73 may be selected such that the clamping element 7 stays in a position if no torque is applied.

As further depicted in FIGS. 3 and 4, the clamping element 7 includes a plurality of engagement recesses 75 in the surface of the first end 7a that are configured to be engaged with the instrument such that torque can be applied with the instrument onto the clamping element 7. In one or more embodiments, the engagement recesses 75 are arranged in pairs on opposite sides of the central axis C and may be offset by 90° from the open upper end of the grooves 73 at the first end 7a of the clamping element 7.

The parts of the bone anchoring device can be made of a bio-compatible material, such as a bio-compatible metal or a bio-compatible metal alloy, for example, stainless steel, titanium, NiTi-alloys, such as Nitinol, magnesium or magnesium alloys, or from a bio-compatible plastic material, such as, for example, polyether ether ketone (PEEK) or poly-1-lactide acid (PLLA). The parts of the bone anchoring device can be made of the same or of different materials.

The instrument will be explained in more detail referring first to FIGS. 1 to 3 and 5 to 8b. The first member 10 includes a tubular portion 11 forming an outer tubular member of the instrument. The tubular portion 11 has a front or distal end 11a and an opposite rear or proximal end 11b. Near the front end 11a of the tubular portion 11, two opposite flat surfaces 12a, 12b are provided that are configured to cooperate with corresponding flat surface portions 58a, 58b of the receiving part 5. The tubular portion 11 further has a portion 13 near the front end 11a with a greater inner diameter than a distance between the flat surfaces 12a, 12b. The portion 13 may widen toward the front end 11a to facilitate placement of the tubular portion 11 over the receiving part 5. A protrusion 14 may be formed at a distance from the front end 11a that may extend circumferentially at an inner wall of the tubular portion 11 and that serves as a stop for limiting insertion of the first end 5a of the receiving part 5 into the tubular portion 11. It shall be noted that the protrusion 14 may form a full annular protrusion or may extend only along a portion of the circumference of the inner wall of the tubular portion 11. The distance of the protrusion 14 from the front end 11a is such that when the tubular portion 11 is placed onto the receiving part 5 and the first end 5a of the receiving part 5 abuts against the protrusion 14, the flat surfaces 12a, 12b can engage the corresponding flat surface portions 58a, 58b of the receiving part.

Offset substantially 90° from the flat surfaces 12a, 12b, two triangular windows 15a, 15b are formed in the wall of the tubular portion 11. The orientation of the triangular windows 15a, 15b is such that the greatest diameter of the triangular windows 15a, 15b faces toward the front end 11a of the tubular portion 11. The windows 15a, 15b allow inspection of the placement of the instrument and may facilitate cleaning of the instrument. A wall thickness of the tubular portion 11 in a region adjacent to the front end 11a extending toward an end portion of the windows 15a, 15b may be increased to increase the strength of the portion of the instrument that engages the receiving part 5. Substantially flat surface portions 16a, 16b are formed at the outer wall of the tubular portion 11 at a position corresponding to the position of the flat surfaces 12a, 12b. The flat surface portions 16a, 16b result in a reduced outer diameter of the tubular portion 11 in a direction perpendicular to the axis of the rod 100 received in the U-shaped recess 52 of the receiving part 5. The flat surface portions 16a, 16b allow use of the instrument in cases where the receiving parts 5 of adjacent bone anchoring devices are positioned very close together.

Adjacent to the rear end 11b, an outer contour of a portion 17 of the tubular portion 11 may be square-shaped. At an end of the square-shaped portion 17 facing away from the rear end 11b, a stop 18 is provided for limiting the axial position of a handle portion on the tubular portion 11 as described below. The stop 18 may be an annular projection. A transverse hole 19 is provided at a distance from the rear end 11b that extends through the wall of the square-shaped portion 17 for receiving a pin 30. The pin 30 has a length such that it can protrude into the interior of the tubular portion 11. The transverse hole 19 is, in a circumferential direction, substantially aligned with a center of the flat surface 12a on one side of the tubular portion 11 (see FIG. 8a).

Turning again to FIGS. 1 to 2b, a handle portion 101 is mounted to the tubular portion 11. The handle portion 101 includes a tubular mounting portion 102 with an inner contour corresponding to the outer contour of the square-shaped portion 17 of the tubular portion 11, such that the handle portion 101 is connectable to the tubular portion 11 via a positive-fit connection. The mounting portion 102 is prevented from moving downwardly or distally toward the front end 11a of the tubular portion 11 by the stop 18. The handle portion 101 extends substantially perpendicular to the tubular portion 11. A transverse hole 103 is provided in the mounting portion 102 at a position offset by 180° from the substantially perpendicularly extending handle portion 101. In the mounted state, the hole 103 in the mounting portion 102 and the hole 19 in the tubular portion 11 are aligned such that the pin 30 can extend through both holes 19, 103.

Figure 10B:
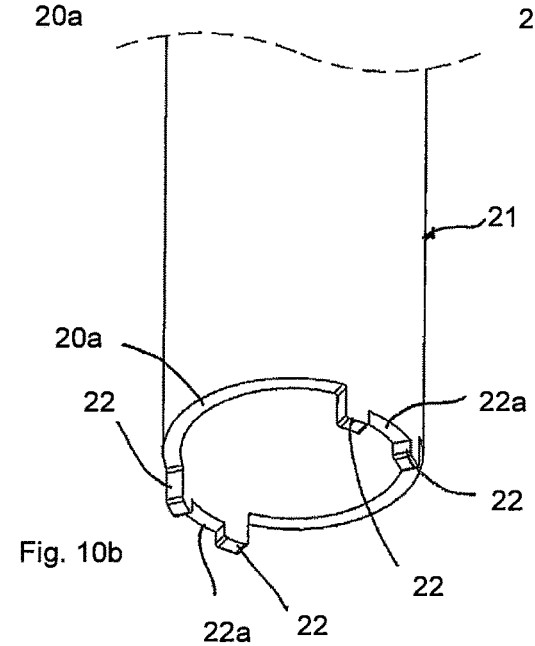

The second member 20 is depicted in more detail in FIGS. 9 to 10b. The second member 20 includes a front end or distal end 20a and a rear end or proximal end 20b. A tubular portion 21 of the second member 20 is provided adjacent the front end 20a. The tubular portion 21 has an outer diameter that is smaller than an inner diameter of the passage 51 in the receiving part 5 such that the tubular portion 21 can be inserted into the receiving part 5 from the first end 5a. An outer diameter of the tubular portion 21 may be substantially the same as an outer diameter of the clamping element 7 at the first end 7a, which can be seen, for example, in FIG. 11b. An inner diameter of the tubular portion 21 is greater than an outer diameter of the first portion 61 of the pressure element 6 such that the tubular portion 21 can slide over the first portion 61 of the pressure element as depicted, for example, in FIG. 11c. In addition, a plurality of engagement projections 22 are provided at the front end 20a of the second member 20. The engagement projections 22 are sized and shaped to engage the recesses 75 provided at the first end 7a of the clamping element 7. In the embodiment shown, four engagement projections 22 are arranged in two pairs that are located on opposite sides of a plane extending through the central axis C. A circumferential distance between two engagement projections 22 of one pair is smaller than a circumferential distance between the two pairs of engagement projections 22. A wall portion 22a between the projections 22 of one pair of projections 22 projects farther than the front end 20a of the tubular portion 21. As a result, when the projections 22 engage the recesses 75 of the clamping element 7, a gap is formed between the first end 7a of the clamping element 7 and the front end 20a of the tubular portion 21 (see FIG. 11b). Thereby, frictional contact between the tubular portion 21 and the clamping element 7 may be avoided.

The second member 20 has a cylindrical portion 23 adjacent to the tubular portion 21. The cylindrical portion 23 can have a solid cross-section (e.g., a cross-section that is not tubular). The cylindrical portion 23 has an outer diameter that is greater than the outer diameter of the tubular portion 21 and smaller than an inner diameter of the tubular portion 11 of the first member 10 such that the cylindrical portion 23 can slide within the tubular portion 11 of the first member 10.

The second member 20 has a longitudinal groove 24 that extends from an end of the cylindrical portion 23 adjacent the tubular portion 21 to a distance from an end of the cylindrical portion 23 opposite the tubular portion 21. The longitudinal groove 24 extends in a direction substantially parallel to the central axis C. A width of the groove 24 is such that a front end of the pin 30 can be guided therein. The groove 24 is located in a circumferential direction substantially in a middle between the two pairs of projections 22. A horizontal recess 25 is provided at the end of the longitudinal groove 24 facing the rear end 20b of the second member The longitudinal groove 24 is open to the horizontal recess 25. In addition, the horizontal recess 25 is longer in the axial direction than the width of longitudinal groove 24. In particular, the length of the horizontal recess 25 in the axial direction is greater than a diameter of the pin 30 such that the pin 30 can move slightly in the axial direction when the pin 30 is in the horizontal recess 25. The horizontal recess 25 extends in a circumferential direction along approximately one quarter of the circumference of the cylindrical portion 23 to less than half of the circumference of the cylindrical portion 23. When viewed in a side view, the longitudinal groove 24 and the horizontal recess 25 together have a substantially inverted L shape.

The longitudinal groove 24 forms a guiding structure configured to guide the insertion of the second member 20 into the tubular portion 11 of the first member 10 such that the position of the projections 22 at the front end 20a is aligned with the position of the recesses 75 of the clamping element 7. The horizontal recess 25 permits rotation of the second member 20 relative to the first member 10, limited by the abutment of the pin 30 against horizontal ends of the horizontal recess 25. The length of the recess 25 in the axial direction allows the pin to move slightly in the recess 25 in the axial direction for locating the recesses 75 of the clamping element 7 and inserting the projections 22 therein.

At the end of the cylindrical portion 23 opposite the tubular portion 21, a post 26 is provided for forming a positive-fit connection with a handle 201. The handle 201 includes a knob 202 that indicates the position of the longitudinal groove 24 in the circumferential direction. Additionally, the knob 202 may 6 internally fix the post 26 to the handle 201.

The instrument is also made of a body compatible material. Examples of such materials may be the same as those described for the bone anchoring device.

The instrument is assembled as follows. The handle portion 101 of the first member is mounted onto the square-shaped portion 16 of the first member such that the holes 19, 103 overlap. Next, the second member 20 is inserted into the tubular portion 11 of the first member 10 from the rear end 11b such that the longitudinal groove 24 is aligned with the holes 19, 103. Finally, the pin 30 is inserted into the holes 19, 103 until the pin 30 protrudes into the longitudinal groove 24 as depicted in FIG. 2b. The knob 202 indicates the position of the longitudinal groove 24.

The use of the instrument will be explained with reference to FIGS. 11a to 11c and FIGS. 12a to 12c. In a first alternative, the bone anchoring device is assembled in-situ such that the bone anchoring element 1 is already inserted into the bone and the receiving part 5 with the pressure element 6 and the clamping element 7 are mounted onto the head 3 thereafter. In a second alternative, the bone anchoring device is assembled outside the human body and the head 3 of the bone anchoring element 1 is inserted manually into the receiving part 5 through the lower opening 56 before the bone anchoring element 1 is anchored to the bone.

The tubular portion 11 of the first member 10 is placed onto the receiving part 5 as depicted in FIGS. 11a and 12a in such a manner that the inner flat surfaces 12a, 12b of the tubular portion 11 engage the flat surface portions 58a, 58b at the outside of the U-shaped recess 52 of the receiving part 5. The first end 5a of the receiving part 5 is received in the tubular portion 11 and abuts against the stop 14 in the tubular portion 11. By means of this, the receiving part 5 is firmly held by the first member 10. The clamping element 7 is arranged around the first portion 61 of the pressure element 6 such that the internal surface 72 of the clamping element 7 does not press onto the flexible portion 63 of the pressure element 6. The recesses 75 of the clamping element 7 are positioned at positions perpendicular to the rod axis.

Then, the second member 20 is inserted into the first member 10 in a position in which the pin 30 can engage the longitudinal groove 24. The tubular portion 21 of the second member 20 is advanced downward (for example, as depicted by the arrow in FIG. 11a). Thereafter, as depicted in FIGS. 11b and 12b, the second member 20 is advanced further downward such that the tubular portion 21 can enter into the receiving part 5. Thereby, the second member 20 is guided in an axial direction by the cooperation of the pin 30 with the longitudinal groove 24. In this configuration, the projections 22 of the second member 20 are aligned with the recesses 75 of the clamping element 7. The second member 20 is advanced downward until the projections 22 enter the recesses 75, and in this relative axial position of the second member 20 relative to the first member 10, the pin 30 has entered the horizontal recess 25 of the second member 20. Finally, as illustrated in FIGS. 11c and 12c, the second member 20 is rotated relative to the first member 10 to apply torque to the clamping element 7. The helical grooves 73 of the clamping element 7 provide guidance for the pins 9a, 9b, such that clamping element 7 is advanced downward. During the downward advancement of the clamping element 7, the internal surface 72 of the clamping element 7 contacts the outer surface of the flexible portion 63 of the pressure element 6 and compresses the flexible portion 63 (i.e., the clamping element 7 provides a clamping force onto the flexible portion 63). Thereby, the pressure exerted onto the head 3 by the pressure element 6 increases. Over advancement of the clamping element 7 is prevented by the end of the horizontal recess 25 which acts as a stop for the pin 30. To decrease the pressure force exerted onto the head 3, the second member 20 can be rotated in a direction opposite to the advancement direction. The first member 10 acts as a counter holding member during the procedure.

Through the above procedure, the frictional fit of the head 3 in the receiving part 5 can be easily and safely increased by rotating the second member 20 relative to the first member 10. After the friction force has been adjusted to a desired amount, first the second member 20 is retracted from the receiving part 5 and then the first member 10 is decoupled from the receiving part 5. The receiving parts 5 of one or more bone anchoring devices can be aligned whereby an angular position of the receiving part 5 relative to the respective bone anchoring element 1 is maintained due to the friction fit. Thereafter the rod 100 is inserted and the bone anchoring devices are fixed by inserting and tightening the locking elements.

Modifications of the above described embodiments are conceivable. The cooperating surfaces on the first member and the receiving part that prevent rotation of the first member relative to the receiving part may be shaped and arranged in a different manner to achieve a positive-fit connection. For example, only one single surface of the receiving part and one single surface of the first member may be sufficient to achieve a positive-fit connection. The engagement portions of the second member and the clamping element may have another shape and/or another arrangement. For example, only one projection and a single corresponding recess may be sufficient. The second member may also be placed around the first member and engage the clamping element from the outside of the receiving part. The longitudinal groove and the horizontal recess may be provided at the first member and a corresponding protrusion at the second member.

With regard to the polyaxial bone anchoring device, another clamping mechanism can be provided. For example, the clamping element can be advanced by a threaded connection between the receiving part and the clamping element. While a bottom loading polyaxial bone anchoring device has been shown, the instrument can also be used with a top loading polyaxial bone anchoring device in which the anchoring element is inserted into the receiving part from the first end. The head of the bone anchoring element may have a design that allows the bone anchoring element with a pressure element adapted thereto to be pivoted only in a single plane. For example, the head may have at least one flat surface portion extending substantially parallel to the shaft axis and the pressure element may have a cooperating portion to limit the pivoting to a single plane. Any design for providing an enlarged pivot angle may also be used. For the locking element all kinds of locking devices can be used, such as bayonet-type locking devices, two-part locking devices that allow clamping the rod and the head independently with two locking elements, outer locking nuts, and the like.

For the bone anchoring element all kinds of bone anchors can be used, such as screws, nails with or without barbs, cannulated bone anchors, two-part bone anchors where head and shank are separate parts that can be assembled, and other bone anchoring elements.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. An instrument for use with a polyaxial bone anchoring device, wherein the polyaxial bone anchoring device includes a receiving part for receiving a rod and for accommodating a head of a bone anchoring element, wherein the head can be clamped by exerting pressure onto it via a clamping element and wherein the pressure can be adjusted using the instrument, the instrument comprising:
a first member comprising a longitudinal axis and a front end having a rigid engagement portion configured to engage the receiving part, wherein at the front end, the rigid engagement portion comprises two diametrically opposite surfaces and a wall that is circumferentially offset 90° from the two diametrically opposite surfaces; and
a second member comprising a front end configured to engage the clamping element and apply torque to the clamping element when the second member is positioned in the first member;
wherein when the second member is positioned in the first member, the second member is movable from a first configuration where the second member is axially displaceable along the longitudinal axis and is restricted from rotational movement relative to the first member, to a second configuration where the second member is rotatable with respect to the first member.

2. The instrument of claim 1, wherein in the second configuration, the second member is rotatable with respect to the first member in a limited angular range around the longitudinal axis less than an entire circumference of the second member.

3. The instrument of claim 2, wherein the limited angular range is less than 180°.

4. The instrument of claim 1, wherein the first member and the second member include cooperating first and second engagement portions, that permit a linear displacement of the second member relative to the first member while limiting rotational movement of the second member relative to the first member.

5. The instrument of claim 4, wherein the first engagement portion includes a longitudinal groove and the second engagement portion includes a protrusion engaging the longitudinal groove.

6. The instrument of claim 4, wherein a third engagement portion is provided that is configured to cooperate with the second engagement portion to permit a rotational movement between the first member and the second member in the second configuration.

7. The instrument of claim 6, wherein the third engagement portion is a horizontal recess that extends substantially perpendicular to the longitudinal axis and wherein the third engagement portion is connected to the first engagement portion.

8. The instrument of claim 1, wherein the first member comprises a stop for limiting an axial movement of the first member relative to the receiving part.

9. The instrument of claim 4, wherein the first and second engagement portions define a mounting position of the second member relative to the first member in an circumferential direction around the longitudinal axis such that when the first engagement portion engages the second engagement portion, the second member is insertable into the first member.

10. The instrument of claim 1, wherein the first member includes a first tubular portion, wherein the second member is insertable into the first tubular portion, and wherein the second member includes a second tubular portion.

11. The instrument of claim 1, wherein the rigid engagement portion of the first member forms a solid annular ring at the front end of the first member.

12. The instrument of claim 1, wherein when the second member is positioned in the first member at an end position where an abutment prevents further movement of the second member towards the front end of the first member, the second member is configured to rotate the clamping element to establish a threaded engagement with the receiving part.

13. A system comprising:
a polyaxial bone anchoring device comprising:
a receiving part having a first end, a second end, a central axis extending through the first end and the second end, a channel for receiving a rod, and an accommodation space for accommodating a head of a bone anchoring element, the accommodation space defining an opening for inserting the head;
a pressure element configured to be arranged at least partially in the accommodation space, the pressure element comprising a flexible portion configured to expand to receive the head of the bone anchoring element; and
a clamping element configured to extend at least partially around the flexible portion of the pressure element and exert a clamping force onto the pressure element, wherein the clamping element is configured to rotate around the central axis; and
an instrument comprising:
a first member comprising a longitudinal axis and a front end having an engagement portion configured to engage the receiving part to prevent rotation of the first member relative to the receiving part; and
a second member comprising a front end having an engagement portion configured to engage an engagement portion of the clamping element and apply torque to the clamping element;
wherein when the second member is positioned in the first member, the second member is movable to rotate the clamping element from a first position to a second position, wherein the clamping element exerts more clamping force onto the pressure element in the second position than in the first position.

14. The system of claim 13, wherein when the clamping element is in the first position, the flexible portion of the pressure element is expandable in the accommodation space, and wherein when the clamping element is in the second position, the clamping element prevents the flexible portion of the pressure element from expanding.

15. The system of claim 13, wherein when the second member is positioned in the first member, the second member is movable from a first configuration where the second member is axially displaceable along the longitudinal axis and is restricted from rotational movement relative to the first member to a second configuration where the second member is rotatable to rotate the clamping element from the first position to the second position.

16. The system of claim 13, wherein the receiving part and the clamping element comprise an advancement structure configured to permit an axial advancement of the clamping element relative to the receiving part when the clamping element is rotated about the central axis.

17. An instrument for use with a polyaxial bone anchoring device, wherein the polyaxial bone anchoring device includes a receiving part for receiving a rod and for accommodating a head of a bone anchoring element, wherein the head can be clamped by exerting pressure onto it via a clamping element and a pressure element, and wherein the pressure can be adjusted using the instrument, the instrument comprising:
a first member comprising a longitudinal axis and a front end configured to engage the receiving part;
a second member comprising a front end configured to engage the clamping element and apply torque to the clamping element when the second member is positioned in the first member;
wherein one of the first and second members comprises a pin, wherein one of the first and second members comprises a groove configured to engage the pin, and wherein the groove has an open end configured to axially receive the pin; and
wherein when the second member is positioned in the first member, the second member is movable from a first configuration where the second member is axially displaceable along the longitudinal axis and is restricted from rotational movement relative to the first member, to a second configuration where the second member is rotatable with respect to the first member.

18. The instrument of claim 17, wherein when the second member is positioned in the first member, the groove is covered by an outer wall of the first member.

19. A method of adjusting a polyaxial bone anchoring device using an instrument, wherein the polyaxial bone anchoring device includes a receiving part for receiving a rod and for accommodating a head of a bone anchoring element, and a clamping element, wherein the head of the bone anchoring element can be clamped by exerting pressure onto it via the clamping element and wherein the pressure can be adjusted using the instrument, the instrument comprising a first member comprising a longitudinal axis and a front end having a rigid engagement portion configured to engage the receiving part, wherein at the front end, the rigid engagement portion comprises two diametrically opposite surfaces and a wall that is circumferentially offset 90° from the two diametrically opposite surfaces, and a second member comprising a front end configured to engage the clamping element and apply torque to the clamping element when the second member is positioned in the first member, the method comprising:
- attaching the rigid engagement portion of the first member of the instrument to the receiving part;
- positioning the second member of the instrument in the first member in a first configuration where the second member is axially displaceable along the longitudinal axis and is restricted from rotational movement relative to the first member; and
- advancing the second member axially towards the front end of the first member to a second configuration where the second member is rotatable with respect to the first member.

20. The method of claim 19, further comprising:
- engaging the clamping element with the second member; and
- rotating the clamping element with the second member from a first position where the head of the bone anchoring element is insertable into the receiving part, to a second position where the clamping element prevents removal of the head from the receiving part.

* * * * *

UNITED STATES PATENT AND TRADEMARK OFFICE
CERTIFICATE OF CORRECTION

PATENT NO. : 9,968,385 B2  
APPLICATION NO. : 15/152032  
DATED : May 15, 2018  
INVENTOR(S) : Lutz Biedermann It is certified that error appears in the above-identified patent and that said Letters Patent is hereby corrected as shown below:

On the Title Page

Item (73), Lines 1-2   delete "BIEDERMAN TECHNOLOGIES GMBH & CO. KG,"  
insert -- BIEDERMANN TECHNOLOGIES GMBH & CO. KG, --

In the Specification

Column 6, Line 1   delete "poly-1-lactide"  
insert -- poly-l-lactide --

Column 7, Line 67   delete "member The"  
insert -- member 20. The --

Signed and Sealed this  
Ninth Day of July, 2019

Andrei Iancu  
*Director of the United States Patent and Trademark Office*